United States Patent
Kurth et al.

(10) Patent No.: US 6,202,384 B1
(45) Date of Patent: Mar. 20, 2001

(54) ARRANGEMENT FOR DEGERMING WEBS OF PACKING FOIL

(75) Inventors: Gunter Kurth; Ingo Sabotka, both of Ranstadt (DE)

(73) Assignee: Hassia Verpackungsmaschinen GmbH, Ranstadt (DE)

( * ) Notice: Subject to any disclaimer, the term of this patent is extended or adjusted under 35 U.S.C. 154(b) by 0 days.

(21) Appl. No.: 09/484,770

(22) Filed: Jan. 18, 2000

(30) Foreign Application Priority Data

Jan. 28, 1999 (DE) .............................................. 199 03 259

(51) Int. Cl.⁷ .................................................. B65B 55/08
(52) U.S. Cl. ................................. 53/141; 53/167; 53/426; 250/455.11; 422/24
(58) Field of Search .............................. 53/141, 167, 425, 53/426; 250/453.11, 454.11, 455.11; 422/24

(56) References Cited

U.S. PATENT DOCUMENTS

| | | | |
|---|---|---|---|
| 3,513,627 | * | 5/1970 | Doucette et al. . |
| 3,933,428 | * | 1/1976 | Egger . |
| 3,947,249 | * | 3/1976 | Egger . |
| 3,994,686 | * | 11/1976 | Ranser et al. . |
| 4,008,401 | * | 2/1977 | Holoubek et al. . |
| 4,011,456 | * | 3/1977 | Bredewater et al. . |
| 4,045,939 | * | 9/1977 | Baumstingl . |
| 4,155,786 | * | 5/1979 | Corbic . |
| 4,175,140 | * | 11/1979 | Bachmann et al. . |
| 4,193,204 | * | 3/1980 | Nerod . |
| 4,297,583 | * | 10/1981 | Nerod . |
| 4,396,582 | * | 8/1983 | Kodera . |

FOREIGN PATENT DOCUMENTS

233332 * 9/1990 (JP) ........................................ 53/425

* cited by examiner

Primary Examiner—John Sipos
(74) Attorney, Agent, or Firm—Collard & Roe, P.C.

(57) ABSTRACT

An arrangement for sterilizing a flat web of a packing foil, which comprises a sterile casing having an inlet and an outlet, a rod-shaped UV radiator disposed in the sterile casing, a guide for guiding the web in a circular path around the UV radiator, the UV radiator being centrally arranged within the circular path and the guide being radially equidistantly spaced from the UV radiator, and deflecting elements at the inlet and the outlet of the sterile casing for deflecting the web into the circular path at the inlet and out of the circular path at the outlet.

9 Claims, 4 Drawing Sheets

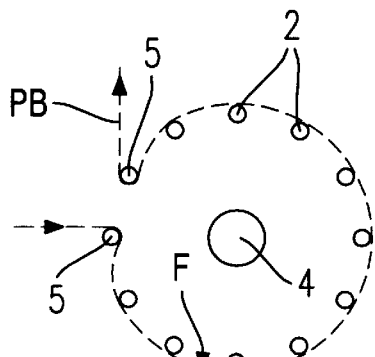
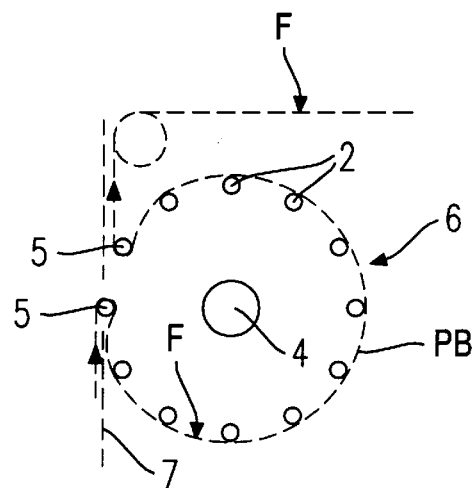
Fig. 5A                    Fig. 5B
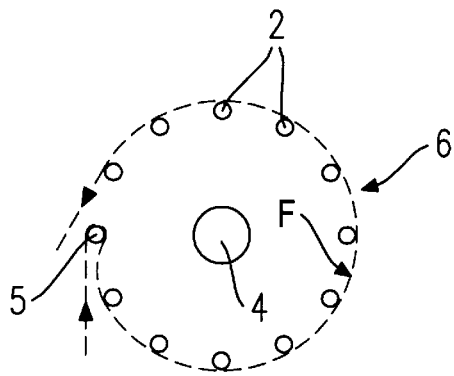
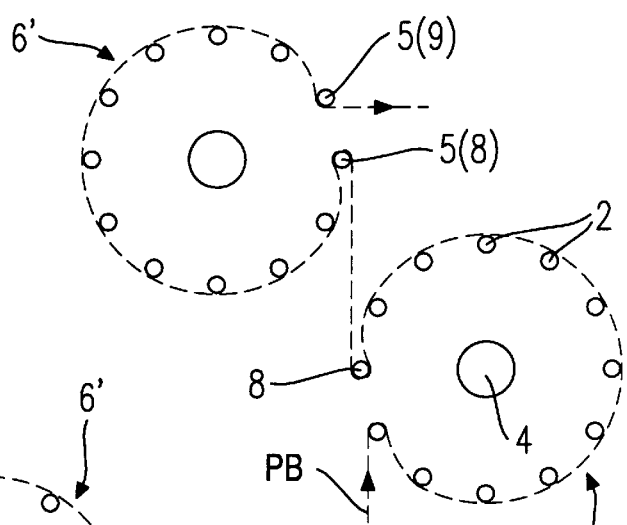
Fig. 5C
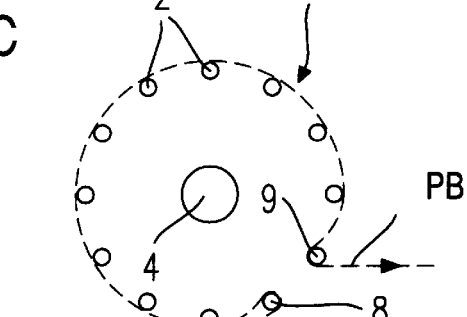
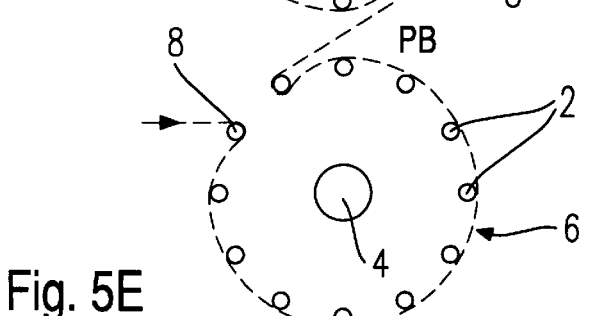
Fig. 5E                    Fig. 5D

ARRANGEMENT FOR DEGERMING WEBS OF PACKING FOIL

BACKGROUND OF THE INVENTION

1. Field of the Invention

This invention relates to new and useful improvements in machines for degerming webs of packing foil. More particularly, the invention relates to means for generating UV-rays along or within which is advanced the web of packing foil discharged from a supply reel for sterilizing purposes to be then fed to a packing machine for further processing thereof while keeping the same sterile, with the term "processing" conveying, for example, molding, loading, closing and separating packings from a strip of packing foil.

2. Description of the Prior Art

The use of UV-radiators for germ reduction also in webs of packing foil corresponding exposed, sterilized and advanced in a so-called disinfecting tube to be subsequently passed through molding, loading and sealing stations of a packing machine, are generally known in the art.

Conventional UV-based degermers for webs of packing foil operate on so-called radiator cassettes linearly arranged along the strip of packing foil, wherein the rear side of the housing accommodating the UV-radiator, for achieving enhanced ray utilization, must be silvered and of a reflector-type design. To insure the required degree of exposure, in addition, either special cassettes of a great width or length are employed or a plurality of smaller-sized cassettes are to be successively arranged along the conveyor track of the web of packing foil equally involving large space-requirements. In view of the operating life of UV-radiators which is limited, as a rule, to about 2000 hours, high replacement costs are involved, in addition, especially high costs are incurred by assembly, maintenance and cleaning operations as well as by the stoppage times involved.

Conventional UV-radiators, in addition, result in considerable ozone generation and, beyond that are likely to have a negative influence on the packing material (pollutant migration).

Water-cooled radiator systems that are also known in the art tend to form condensate once the dew point is fallen below which is likely to result in a direct reduction of the UV-exposure of the packings and also in an indirect reduction of exposure as a consequence of corrosive effects on the reflector faces.

SUMMARY OF THE INVENTION

It is the object of the invention to provide a means for degerming webs of packing foil by employing a UV-radiator requiring no radiation reflectors, with the said means involving low space requirements despite a relatively large exposure surface of the web of packing foil, with the surface exposed being adapted to be well protected and enclosed, thereby insuring a uniform intensity of exposure of the web of packing foil advanced therealong, at the same time maintaining a high density and enabling, in an extremely simple way, the "bare" radiator free from a cassette or housing to be associated to the web of packing foil to be exposed and, hence, permitting worn-out radiators to be easily and quickly replaced by new ones.

These requirements, in the practice of the invention, are complied with by a degermer in that a UV-radiator of rod-type design is centrally arranged between guiding elements for the web of packing foil disposed at an equidistant radial distance about the UV-ray generator, with web deflecting members being associated at the inlet and/or outlet sides to the web supply track of a substantially circular configuration as defined by the said elements, with the web deflecting members feeding the web of packing foil into or out of the circular supply track.

The "and/or"-options (yet to be explained in closer detail hereinafter) merely result from different alternatives of feeding or introducing the web of packing foil into or out of the track of exposure. Thanks to the configuration of the degermer according to the invention a highly constricted yet relatively extended track of exposure is provided to which the centrally located UV-radiator held in an easy-to-mount way on one end only, without any reflectors, will radially and circumferentially release its rays with full and uniform density.

Basically, in the practice of the invention, initially, only one side of the web of packing foil is exposed to radiation, namely the side which, subsequently, gets into contact, in the packing machine, with the material to be loaded. The reason for this resides in that webs of packing foil also are advanced and processed in sterile semi-cylindrical tubes in the adjoining packing machine so that the other side of the strip of foil need not be sterile. Semi-cylindrical tubes of this type held sterile are being used, in particular, in deep-drawing machines.

However, as packing machines having sterile full-cylindrical tubes, i.e. sterile tubes completely enclosing the web of packing foil passing therethrough, involve less structural efforts, an advantageous and preferred embodiment of the device of the invention resides in that associated to the circular track of supply and exposure is another circular supply track, with one of the said tracks being provided with feed-in deflection elements and the other of said tracks being provided with discharge deflection elements. In other words, this constitutes a quasi S-type guidance of the packing foil to be degermed on both sides, wherein the strip of packing foil discharged from the first supply track and degermed on one side, with the side not yet degermed, now faces the UV-radiator in the following exposure track, in order to be fed into the directly following supply track in which the UV-radiator equally arranged centrally will act upon the side of the web of packing foil not yet degermed.

Apart from this directly neighbored association of two such circular tracks of supply and exposure to be successively passed by the web of packing foil it will be readily possible (yet to be explained hereinafter in greater detail) to provide two or more of such pairs of supply tracks in successive relationship should this be necessary, depending on the desired or required degree of sterilization.

The guiding elements defining the circular guidance of the web of packing foil can be made of rod-type rolling members; alternatively, they can be in the form of a cylinder of UV-permeable material.

Other objects and advantages of the invention will appear more fully hereinafter as the description proceeds, with reference to the accompany drawings.

BRIEF DESCRIPTION OF THE DRAWINGS

FIGS. 5A to 5E schematically show, omitting the sterile housing, different inlet and outlet guides of the web of packing foil leading into and out of the circular tracks of supply and exposure;

DESCRIPTION OF THE PREFERRED EMBODIMENTS

Figure 1:
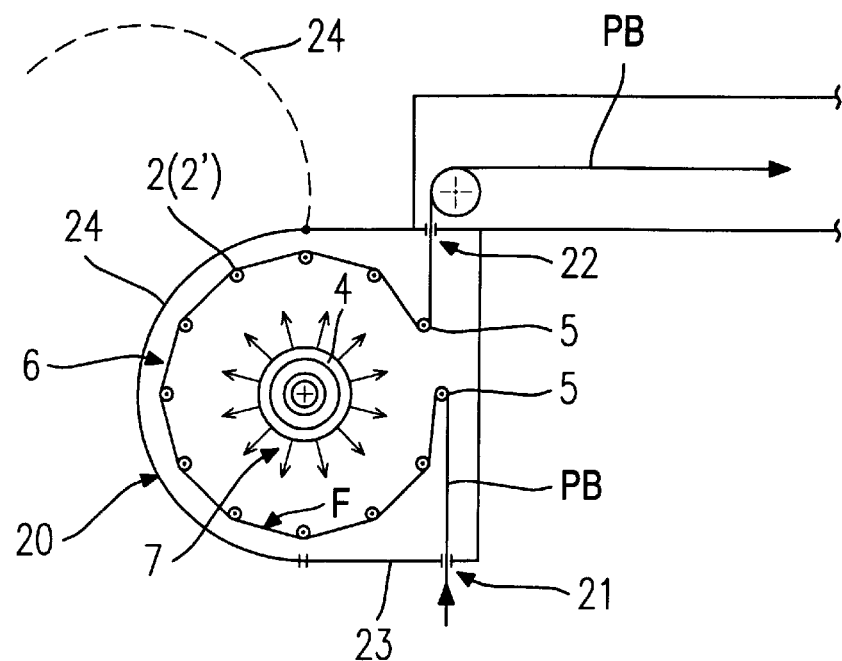
FIG. 1 shows the principle of the circular guidance of the web of packing foil within a sterile casing about a centrally arranged UV-radiator.

The arrangement of the invention for degerming webs of packing foil PB comprises means 1 for the generation of UV-rays and guiding elements 2 for advancing the webs of packing foil PB along a UV-radiator 4. The guiding elements 2 and the UV-radiator 4 are accommodated within a sterile casing 20 provided with inlet and outlet ports 21,22 and being under a slight excess pressure of a gaseous sterile agent, such as sterile air, to prevent the ingress of germs from the atmosphere from occurring.

Now, it is of importance to an arrangement of the afore-described type that the UV-radiator 4 of rod-shaped configuration be centrally arranged between the guiding elements 2 located at an equidistant radial distance about the UV radiator 4. Associated with the circular supply track 6 conveying the web of packing foil defined by the guiding elements 2, at the inlet and/or outlet, are packing web deflecting elements 5 leading the web of packing foil BP into and out of the circular track of supply. In the embodiment according to FIG. 1 the guiding elements 2 are formed of rod-shaped rollers 2' of small diameters rotably arranged within the walls 23 of the sterile casing 20, whereas in the embodiment according to FIG. 2 they comprise a cylinder "2 made of UV-permeable material. The cylinder 2" may be rotably arranged although this is not imperative.

Figure 2:
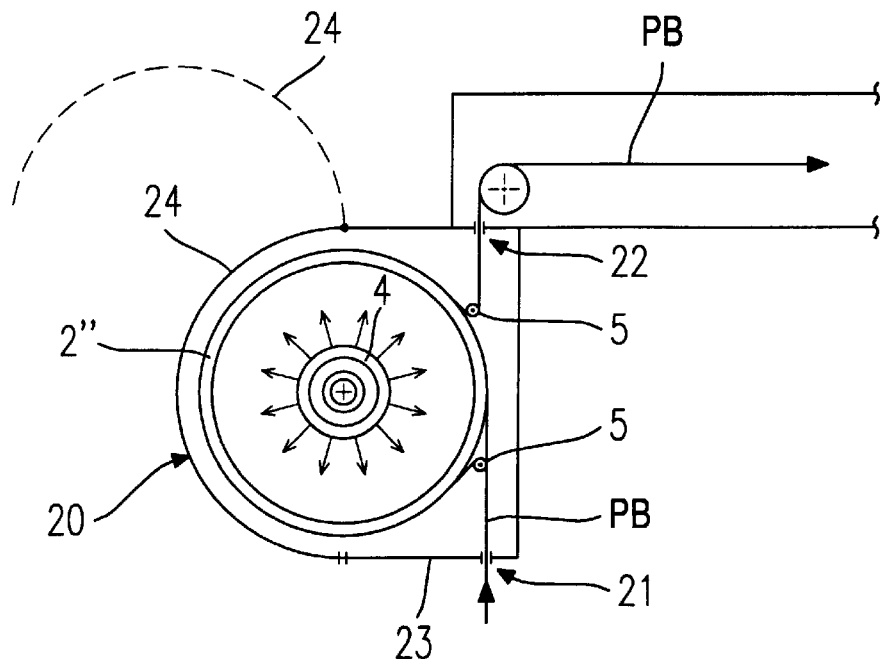
FIG. 2 is a view corresponding to the one of FIG. 1 wherein the guiding elements are of different designs.

As shown in FIGS. 1, 2, only one side F of the web of packing foil BP is exposed to radiation, namely the one which subsequently gets into contact, within the packing machine, with the item to be loaded. The sterile casing 20 preferably is provided with a wall portion 24 to be opened which, in the opening position, is shown in broken lines in FIGS. 1 to 3, with the latter figure showing it on both sides of the casing 20'. With the wall portions 24 opened, the web of packing foil PB readily can be placed by hand about the guiding elements 2 to be then drawn into the adjoining packing machine. The wall section 24 may be, as opposed to the illustration, in the form of a simple lid removable from the casing 20.

Figure 3:
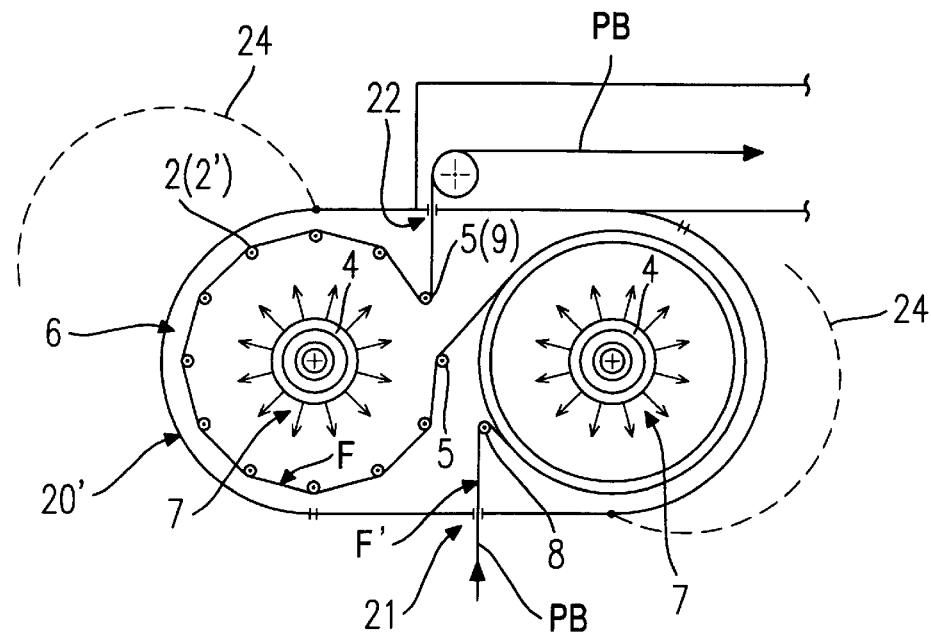
FIG. 3 schematically shows a combination of the assemblies according to FIGS. 1, 2.

In the embodiment according to FIG. 3, the two arrangements according to FIGS. 1, 2 are combined with one another in order to enable the two sides F, F' of the web of packing foil to be exposed to radiation; this will not require any closer explanation as it is readily understood from the illustrated guidance of the web of packing foil. It should be noted that such an association in pairs of assemblies within a common casing 20' is also possible by employing two assemblies of the type as shown in FIGS. 1 or 2.

Figure 4:
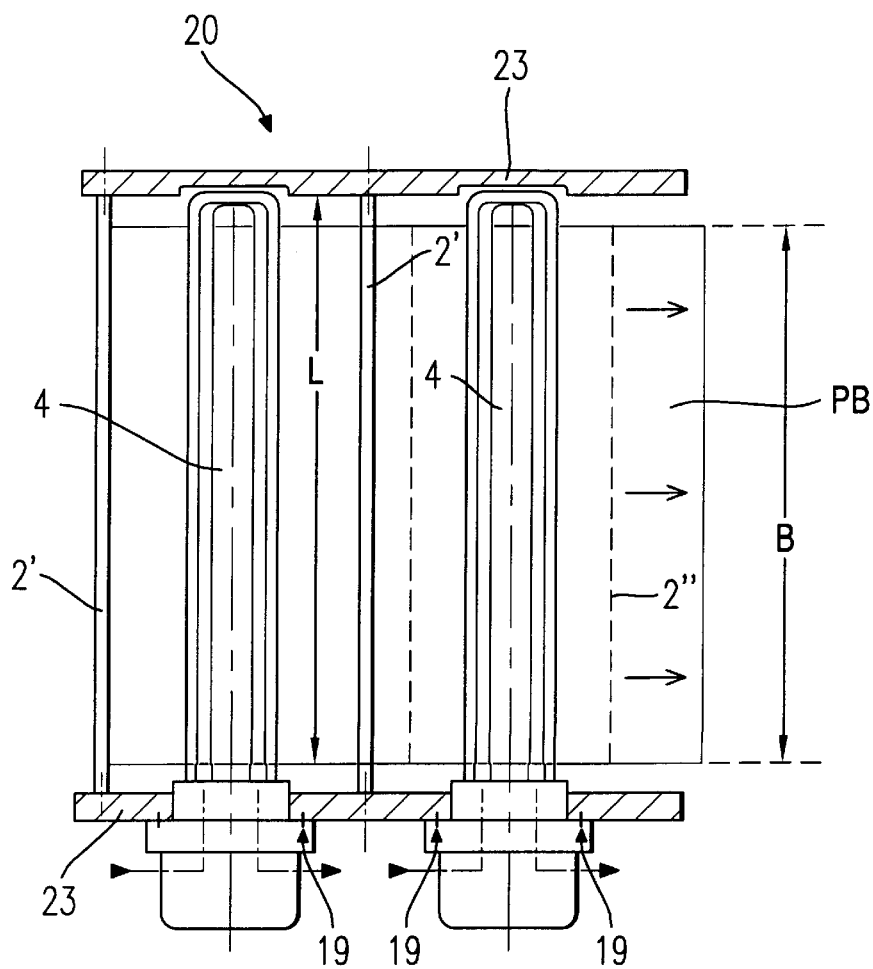
FIG. 4 schematically shows a plan view of the embodiment according to FIG. 3.

FIG. 4 schematically shows a sectional view of the embodiment according to FIG. 3 also revealing the rod-type configuration of the UV-radiator 4 the length L of which substantially corresponds to the width B of the web of packing foil BP.

The radiators 4, which can also be cooling radiators, are suitably arranged within one of the side walls 23 of the sterile housing 20 and are mounted on holding elements 19 in a replaceable way, i.e. they are easy to mount and easy to replace once their operating life has ended. No power connectors have been illustrated as they are known in the art.

A large variety of options are available for feeding the web of packing foil into the assembly of the invention and for passing the same from the assembly to the adjoining packing machine. Some of them are shown in FIGS. 5A to 5E Among these options special reference is made to the one of FIG. 5B in which the elements 5 deflecting the web of packing foil are arranged substantially along a straight line 7 contacting the circular track 6. However, virtually, this will be determined by the design at the inlet side of the packing machine coupled to the arrangement.

In the examples showing the guidance of the web of packing foil according to FIGS. 1, 2 and 5A through 5C, the web of packing foil PB passing along the substantially circular supply track 6 only on one side is exposed to UV-radiation; the exposed face F then forms, in the packing machine, the face of the packing foil on the side of the material to be loaded, i.e. the side to be degermed.

However, for the reasons set out in the afore-going it is preferred to expose both sides of the web of packing foil PB to radiation and sterilization. In reference to FIGS. 3,4 and 5 D,5 E, another circular track 6' is associated to the circular supply track 6, with the latter being provided with feed-in elements 8 and track 6' being provided with discharge deflecting elements 9.

Figure 6:
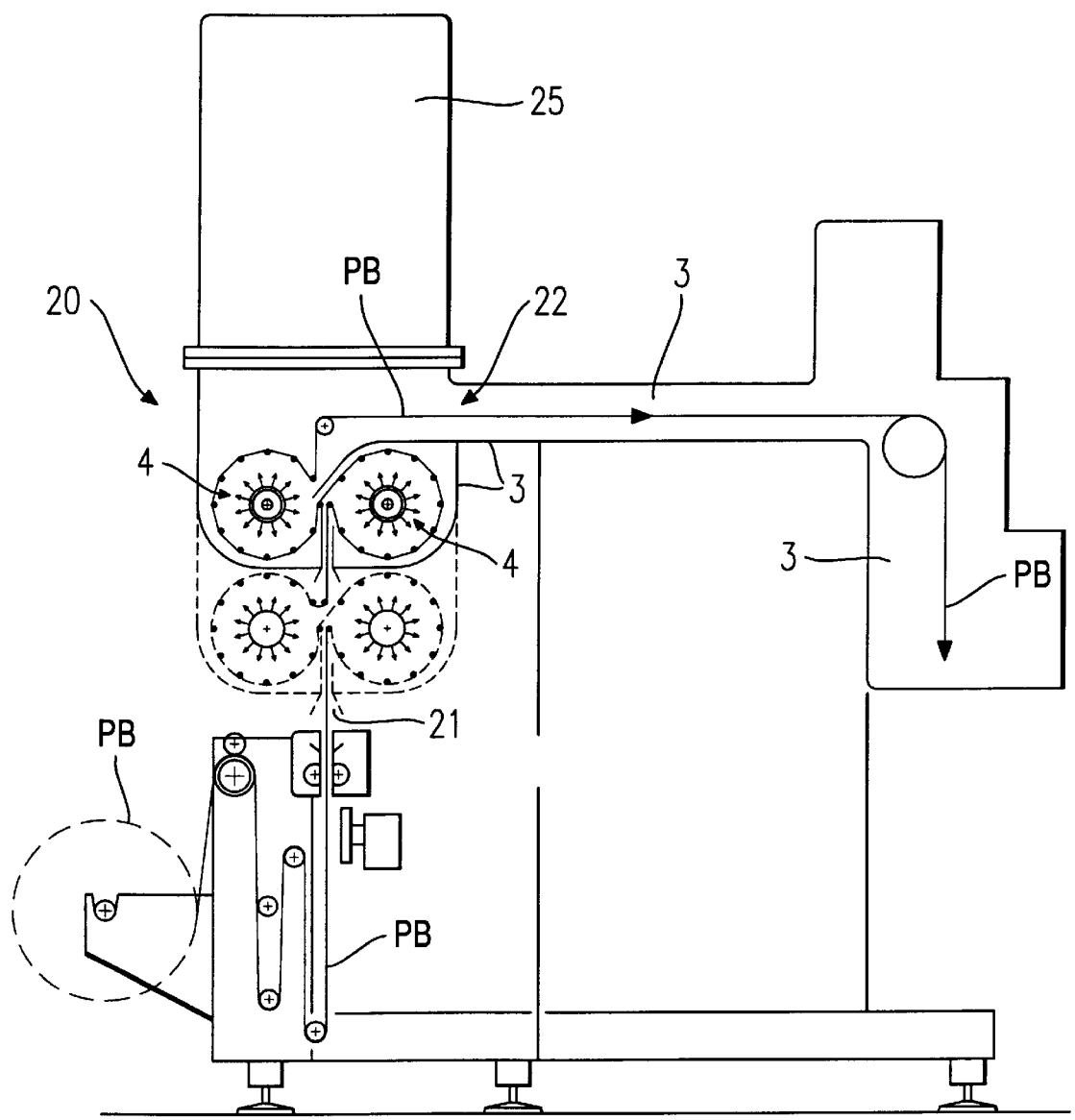
FIG. 6 schematically shows the arrangement of the invention in connection and association with a packing machine shown, by way of example, in contours only.

In case of need, also multiple pairs of associated supply tracks 6,6' along the track feeding the web of packing foil to the packing machine will be possible as shown by FIG. 6 illustrating an example of double pairing and showing, at the same time, an example of associating the arrangement to the degermed and cylindrical tube 3 of a packing machine otherwise only schematically shown, which in the present instance is a machine for making tubular bags. In that form of embodiment, a sterile air generator 25 is arranged above the casing 20 of the degermer of the invention. The said sterile air generator 25, hence, not only supplies sterile air, under a slight excess pressure, to the arrangement but also to the cylindrical tube 3 of the packing machine which, as shown, is directly connected to the outlet port 22 of the sterile casing 20.

A deep-drawing packing machine, the supply track and, hence, the web of packing foil of which is held sterile only on one side at the top thereof by a semi-cylindrical tube has not been illustrated. In respect of such a machine, assemblies of the type as shown in FIGS. 1,2 will be used, i.e. devices provided with guides for guiding the web of packing foil as shown in FIGS. 5A through 5C, because in semi-cylindrical tubes the non-sterilized side of the web of packing foil BP is not directed to the interior of the semi-cylindrical tube.

No separate conveyor elements are required by the web of packing foil PB in the assembly of the invention as the web of packing foil PB to be degermed is drawn by the conveyor elements within the adjoining packing machine through the assembly at the operating cycle of the packing machine.

Any changes may be made to the construction of the device and the arrangement of parts from those described without departing from the spirit of the invention, provided, however, that such changes fall within the scope of the claims appended hereto:

What we claims is:

1. An arrangement for degerming a flat web of a packing foil, which comprises
(a) a sterile casing having an inlet and an outlet,
(b) a rod-shaped UV radiator disposed in the sterile casing, (c) guide means for guiding the web in a circular path around the UV radiator, the UV radiator being centrally arranged within the circular path and the guide means being radially equidistantly spaced from the UV radiator, and (d) deflecting elements at the inlet and the outlet of the sterile casing for deflecting the web into the circular path at the inlet and out of the circular path at the outlet.

2. The arrangement of claim 1, wherein the guide means is stationarily positioned within the sterile casing.

3. The arrangement of claim 2, wherein the guide means is comprised of a series of rotatable rollers.

4. The arrangement of claim 2, wherein the guide means is comprised of a rotatable cylinder of UV-permeable material.

5. The arrangement of claim 1, wherein the UV radiator has a length corresponding to the width of the web.

6. The arrangement of claim 1, wherein the sterile casing has a wall section which may be opened.

7. The arrangement of claim 1, wherein the deflecting elements are arranged substantially along a rectilinear tangent of the circular path.

8. The arrangement of claim 1, wherein the sterile casing has a circular wall portion extending concentrically about the circular path.

9. The arrangement of claim 1, comprising another rod-shaped UV radiator disposed in the sterile casing, another guide means for guiding the web in a circular path around the other UV radiator, the other UV radiator being centrally arranged within the latter circular path and the other guide means being radially equidistantly spaced from the other UV radiator, and further deflecting elements for deflecting the web from the first-named circular path into the latter circular path.

* * * * *